(12) United States Patent
Liao

(10) Patent No.: US 7,414,408 B2
(45) Date of Patent: Aug. 19, 2008

(54) THIN DECK WATER PROPERTY SENSOR

(76) Inventor: Yi-Chia Liao, No. 3-6, Xinzhuang, Baishou Village, Shitan Shiang, Miaoli County (TW)

( * ) Notice: Subject to any disclaimer, the term of this patent is extended or adjusted under 35 U.S.C. 154(b) by 0 days.

(21) Appl. No.: 11/603,033

(22) Filed: Nov. 22, 2006

(65) Prior Publication Data

US 2008/0116069 A1 May 22, 2008

(51) Int. Cl.
*G01N 27/02* (2006.01)
*G01R 27/08* (2006.01)

(52) U.S. Cl. .................. 324/439; 324/693; 324/694

(58) Field of Classification Search ............... 324/439, 324/693, 694
See application file for complete search history.

(56) References Cited

U.S. PATENT DOCUMENTS 6,222,371 B1 * 4/2001 Snyder ................. 324/439
6,605,947 B2 8/2003 Liao
6,824,394 B1 * 11/2004 Brundage ................ 439/65
2006/0070429 A1 * 4/2006 Liao ..................... 73/64.53

\* cited by examiner

*Primary Examiner*—Timothy J Dole
(74) *Attorney, Agent, or Firm*—Muncy, Geissler, Olds & Lowe, PLLC

(57) ABSTRACT

A thin deck water property sensor includes a base, an upper lid, a positive and negative probe, an electric connection element, a processing unit and a display unit. The base and the upper lid are coupled together to form a flat deck. The upper lid has a recess to hold sample water to be tested. The positive and negative probe is extended into the recess in contact with the sample water. The electric connection element has one end connecting to the processing unit and another end coupling with a conductive elastic member. The conductive elastic member is connected to the positive and negative probe. The processing unit receives charged signals of the sample water to generate a test result which is displayed on the display unit.

5 Claims, 4 Drawing Sheets

THIN DECK WATER PROPERTY SENSOR

FIELD OF THE INVENTION

The present invention relates to a water property sensor and particularly to a thin deck water property sensor that is portable and easy to carry and use.

BACKGROUND OF THE INVENTION

With the living standard of people increased people have a greater awareness of health improvement. Drinking water is one of the important factors that affects the health of people. U.S. Pat. No. 6,605,947, referring to FIGS. 1 and 2, discloses an apparatus to detect water property. It includes a seat 1, a cup body 2, a measuring body 3 and a display 4. The seat 1 has a handle 5 extending upwards. The handle 5 has a latch portion 6 on the top end. The cup body 2 is rested on the seat 1 with the edge of the cup body 2 latched by the latch portion 6. The cup body 2 contains a liquid and has at least one probe 7 on the inner wall in contact with the liquid. The measuring body 3 is located in the handle 5 to be electrically connected to the probe 7 to measure the resistance parameters of the liquid. The display 4 is located on the top side of the handle 5 and connected to the measuring body 3 to display the measured results. Thereby the property of the liquid contained in the cup body 2 such as concentration, pH value and parameters of sweetness and saltiness can be tested and detected.

While the conventional technique mentioned above can detect water property, the cup body 2 and the measuring body 3 are different elements and separated. They have to be coupled together when in use. If one of them is lost, it becomes useless. Moreover, it is quite bulky and not easy to carry. All this creates problems in use, thus cannot meet user's requirements.

SUMMARY OF THE INVENTION

Therefore the primary object of the present invention is to provide a thin deck water property sensor that is portable and easy to carry and use.

The thin deck water property sensor according to the invention includes a base, an upper lid, a positive and negative probe, an electric connection element, a processing unit, a display unit and a power supply unit. The power supply unit supplies required electric power to the processing unit and the display unit. The base and the upper lid are coupled to form a flat deck which has a housing compartment to hold the processing unit and the power supply unit. The upper lid has a recess. The positive and negative probe is extended from the housing compartment to the recess. The processing unit is connected to one end of the electric connection element which has another end coupled with a conductive elastic member. The conductive elastic member is connected to the positive and negative probe. The display unit and the processing unit are connected to the upper lid and exposed thereon.

By means of the construction set forth above, the recess can hold sample water which is in contact with the positive and negative probe so that the sample water is measured and tested. The processing unit generates a test result which is displayed on the display unit.

The foregoing, as well as additional objects, features and advantages of the invention will be more readily apparent from the following detailed description, which proceeds with reference to the accompanying drawings.

DETAILED DESCRIPTION OF THE PREFERRED EMBODIMENT

Figure 1:
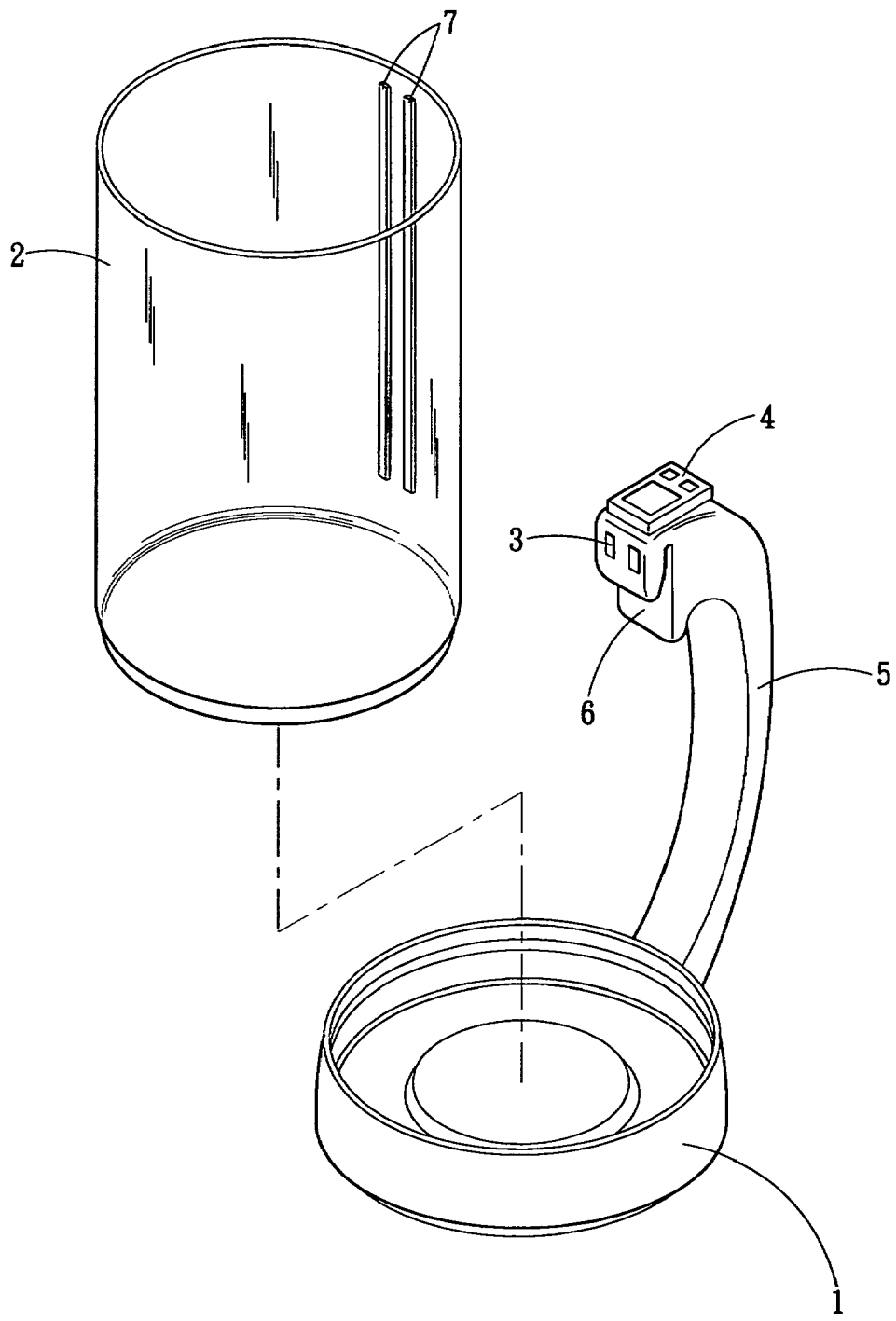
FIG. 1 is an exploded view of a conventional water property sensor.
Figure 2:
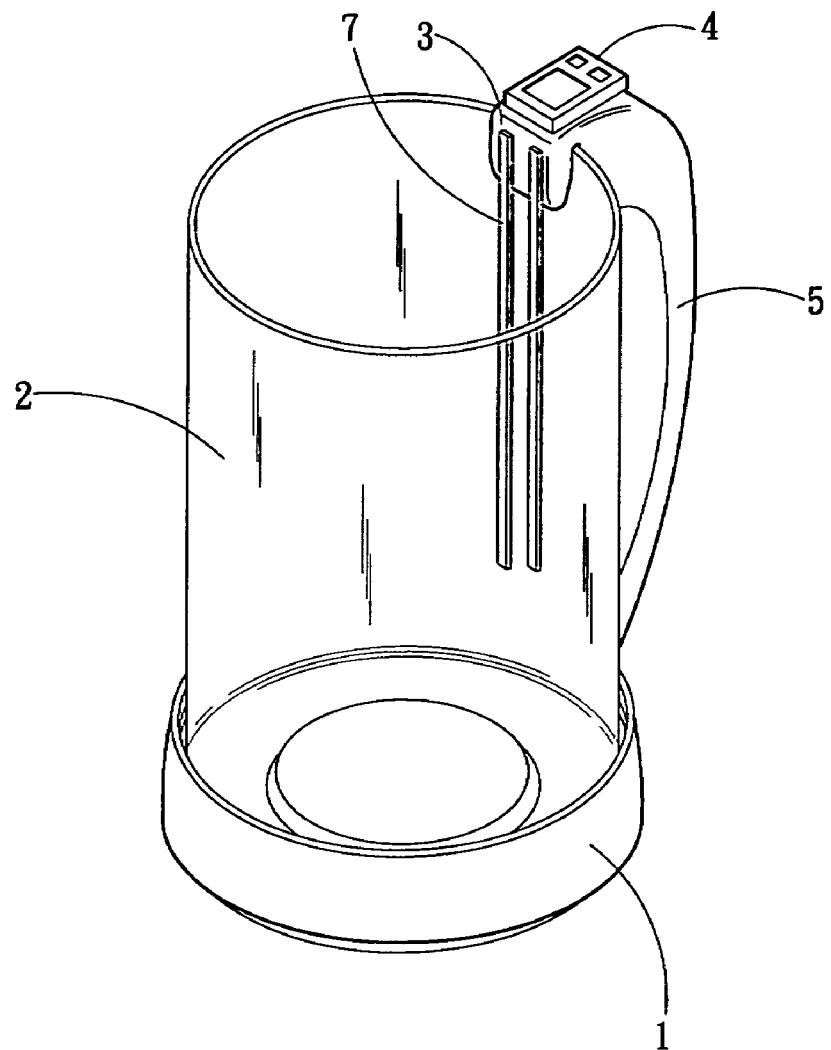
FIG. 2 is a perspective view of a conventional water property sensor.
Figure 3:
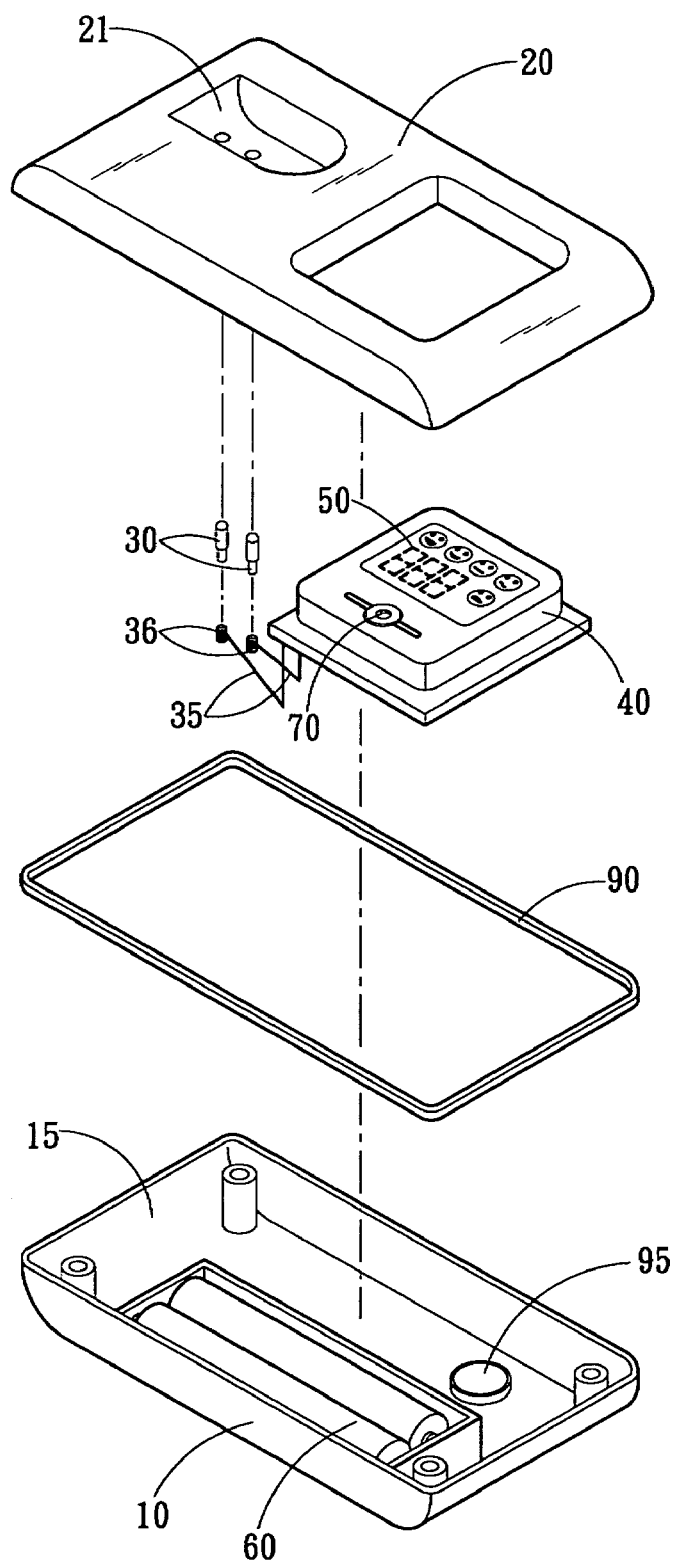
FIG. 3 is an exploded view of the water property sensor of the invention.
Figure 4:
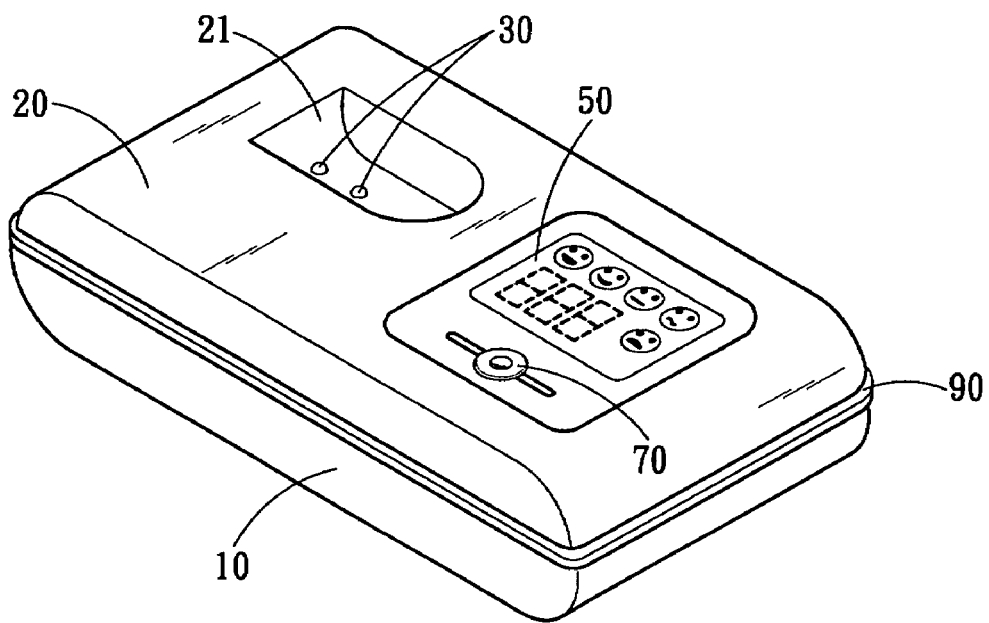
FIG. 4 is a perspective view of the water property sensor of the invention.

Please refer to FIGS. 3 and 4, the thin deck water property sensor according to the invention aims to test the property of sample water. It includes a base 10, an upper lid 20, a positive and negative probe 30, a processing unit 40, a display unit 50 and a power supply unit 60. The base 10 and the upper lid 20 are coupled together to form a flat deck which has a housing compartment 15. The upper lid 20 has a recess 21 to hold the sample water.

The positive and negative probe 30 is extended from the housing compartment 15 to the recess 21. The processing unit 40 is held in the housing compartment 15 and is connected to one end of an electric connection element 35 which has another end coupled with a conductive elastic member 36. The conductive elastic member 36 may be an elastic reed or a spring or the like that is elastic and electric conductive. The conductive elastic member 36 is connected to the positive and negative probe 30. The processing unit 40 tests the sample water and generates a test result.

The display unit 50 and the processing unit 40 are connected and exposed on the upper lid 20 to display the test result. The power supply unit 60 is held in the housing compartment 15 to provide electric power required by the processing unit 40 and the display unit 50. Thus users can know water property according to the test result.

The display unit 50 can display various graphics such as different facial pictures to indicate different water property based on preset test standards. Thereby users can be informed of the water property quickly through the graphics. The display unit 50 may also be an LCD device to directly display different test result in numeric values, or by text such as GOOD, FAIR, BAD, or in graphics to enable users to know water property quickly.

The invention may further include a power reset button 70 to save the power of the power supply unit 60. After the power supply unit 60 has been set ON for a period of time, the power supply of the power supply unit 60 can be cut off. The power reset button 70 aims to activate the power supply unit 60 after it has been cut off to start power supply. When the power supply unit 60 is in operation, the power reset button 70 can be used to reset the system to enable users to perform water property test at the next time.

The invention may also include a water-proof element 90 on the coupling juncture of the base 10 and the upper lid 20. The water-proof element 90 may be a water-proof strip made from rubber to prevent water from seeping into the housing compartment 15 to ensure that the invention can function properly. The base 10 and the upper lid 20 may also be coupled together through a water-proof layer formed by high frequency fusion to replace the water-proof element 90 to prevent water seeping. The invention may further include a buzzer 95 in the housing compartment 15 connecting to the processing unit 40. When the power supply reset button 70 is maneuvered by users, the buzzer 95 generates sound to confirm operation.

When the invention is in use, pour the sample water to be tested in the recess 21, the test result can be obtained and displayed on the display unit 50. Water property may be indicated through different graphics. The thin deck of the invention can be formed in a small size like a name card, thus is portable and easy to carry and use.

What is claimed is:

1. A thin deck water property sensor to test water property of a sample water, comprising:
   a base;
   an upper lid which is coupled with the base to form the deck and a housing compartment, and has a recess to hold the sample water;
   a positive and negative probe which is located in the housing compartment and extended into the recess;
   a processing unit held in the housing compartment;
   an electric connection element which has one end connecting to the processing unit and another end coupling with a conductive elastic member, the conductive elastic member being connected to the positive and negative probe to allow the processing unit to test the sample water and generate a test result;
   a display unit which is connected to the processing unit and exposed on the upper lid to display the test result in graphics according to a preset test standard;
   a power supply unit which is held in the housing compartment to supply electric power required by the processing unit and the display unit, and cuts off the electric power supply after having continuously supplied for a selected time period;
   a power reset button to activate the electric power supply of the power supply unit and reset the system when the electric power supply of the power supply unit has been activated, and the base and the upper lid being interposed by a water-proof layer formed by high frequency fusion.

2. The thin deck water property sensor of claim 1, wherein the display unit is an LCD (liquid crystal display).

3. The thin deck water property sensor of claim 1, wherein the conductive elastic member is an elastic reed.

4. The thin deck water property sensor of claim 1, wherein the conductive elastic member is a spring.

5. The thin deck water property sensor of claim 1 further having a buzzer located in the housing compartment and connected to the processing unit.

* * * * *